(12) United States Patent
Ginn et al.

(10) Patent No.: US 6,663,655 B2
(45) Date of Patent: Dec. 16, 2003

(54) APPARATUS AND METHODS FOR SEALING VASCULAR PUNCTURES

(75) Inventors: Richard S. Ginn, San Jose, CA (US); Stephen M. Salmon, Napa, CA (US)

(73) Assignee: Core Medical, Inc., Sunnyvale, CA (US)

( * ) Notice: Subject to any disclaimer, the term of this patent is extended or adjusted under 35 U.S.C. 154(b) by 152 days.

(21) Appl. No.: 09/866,548

(22) Filed: May 25, 2001

(65) Prior Publication Data

US 2002/0077657 A1 Jun. 20, 2002

Related U.S. Application Data

(63) Continuation-in-part of application No. 09/738,431, filed on Dec. 14, 2000.

(51) Int. Cl.$^7$ ................................................ A61B 17/08
(52) U.S. Cl. ........................................................ 606/213
(58) Field of Search .................................. 606/232, 213

(56) References Cited

U.S. PATENT DOCUMENTS

| | | |
|---|---|---|
| 287,046 A | 10/1883 | Norton |
| 2,969,887 A | 1/1961 | Darmstadt et al. |
| 3,015,403 A | 1/1962 | Fuller |
| 3,944,114 A | 3/1976 | Coppens |
| 4,525,157 A | 6/1985 | Vaillancourt |
| 4,738,658 A | 4/1988 | Magro et al. |
| 4,744,364 A | 5/1988 | Kensey |
| 4,852,568 A | 8/1989 | Kensey |
| 4,878,915 A | 11/1989 | Brantigan |
| 5,015,247 A | 5/1991 | Michelson |
| 5,021,059 A | 6/1991 | Kensey et al. |
| 5,032,125 A | 7/1991 | Durham et al. ................ 606/62 |
| 5,061,274 A | 10/1991 | Kensey |
| 5,114,032 A | 5/1992 | Laidlaw |
| 5,192,301 A | 3/1993 | Kamiya et al. |
| 5,192,302 A | 3/1993 | Kensey et al. |
| 5,222,974 A | 6/1993 | Kensey et al. |
| 5,275,616 A | 1/1994 | Fowler |
| 5,290,310 A | 3/1994 | Makower et al. |
| 5,292,332 A | * 3/1994 | Lee .............................. 606/213 |
| 5,306,254 A | 4/1994 | Nash et al. |
| 5,320,639 A | 6/1994 | Rudnick |
| 5,334,216 A | 8/1994 | Vidal et al. |
| RE34,866 E | 2/1995 | Kensey et al. |
| 5,411,520 A | 5/1995 | Nash et al. |
| 5,425,757 A | 6/1995 | Tiefenbrun et al. ........... 623/66 |
| 5,486,195 A | 1/1996 | Myers et al. |
| 5,522,840 A | 6/1996 | Krajicek |
| 5,571,181 A | 11/1996 | Li ................................ 623/11 |
| 5,645,565 A | 7/1997 | Rudd et al. |
| 5,690,674 A | 11/1997 | Diaz |

(List continued on next page.)

OTHER PUBLICATIONS

M. Saines, PCT Publication No. WO 00/71032 A2, "Hemostatic Device for Angioplasty", Nov. 30, 2000.

Primary Examiner—Gary Jackson
(74) Attorney, Agent, or Firm—Orrick, Herrington & Sutcliffe LLP; James W. Geriak

(57) ABSTRACT

An apparatus for sealing a passage through tissue includes a bioabsorbable body disposed on a distal end of a handle device. The plug member includes a helical thread on its outer surface and the plug member and handle device include cooperating lumens communicating with a distal port. A sealing member is disposed within the plug member lumen. An obturator is inserted through the lumens until its distal tip extends beyond the plug member, the distal tip including a bleed back port. The plug member is threaded into a passage towards a blood vessel until the bleed back indicator identifies the location of the vessel with respect to the plug member. The plug member is released from the handle device, the handle device and obturator are withdrawn, and the sealing member seals the lumen. The plug member is left within the passage to seal the passage until the tissue heals.

61 Claims, 7 Drawing Sheets

U.S. PATENT DOCUMENTS

| | | |
|---|---|---|
| 5,728,116 A | 3/1998 | Rosenman .................. 606/151 |
| 5,728,122 A | 3/1998 | Leschinsky et al. |
| 5,871,474 A | 2/1999 | Hermann et al. |
| 5,871,501 A | 2/1999 | Leschinsky et al. |
| 5,871,525 A | 2/1999 | Edwards et al. |
| 6,016,806 A | 1/2000 | Webb .......................... 128/846 |
| 6,082,362 A | 7/2000 | Webb .......................... 128/846 |
| 6,296,657 B1 | 10/2001 | Brucker ...................... 606/213 |

\* cited by examiner

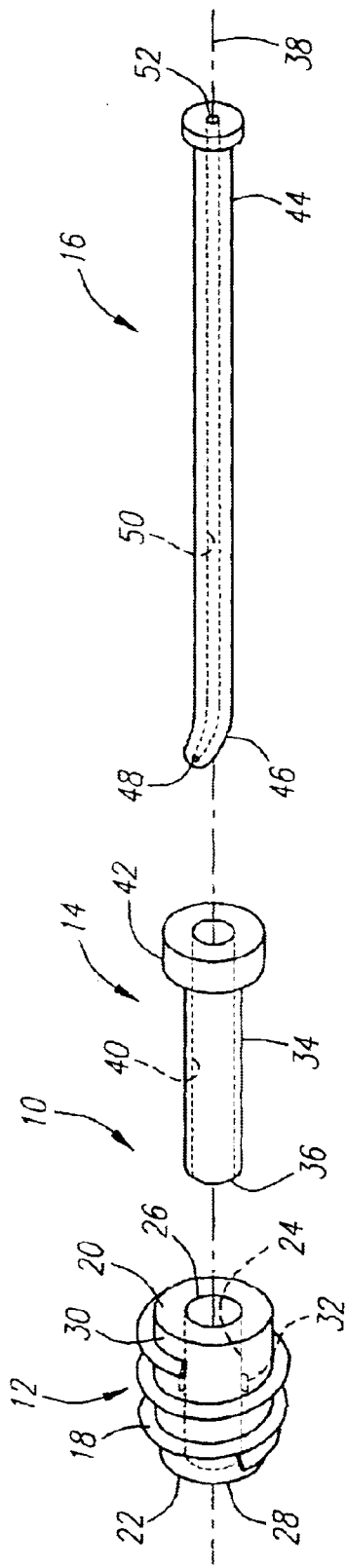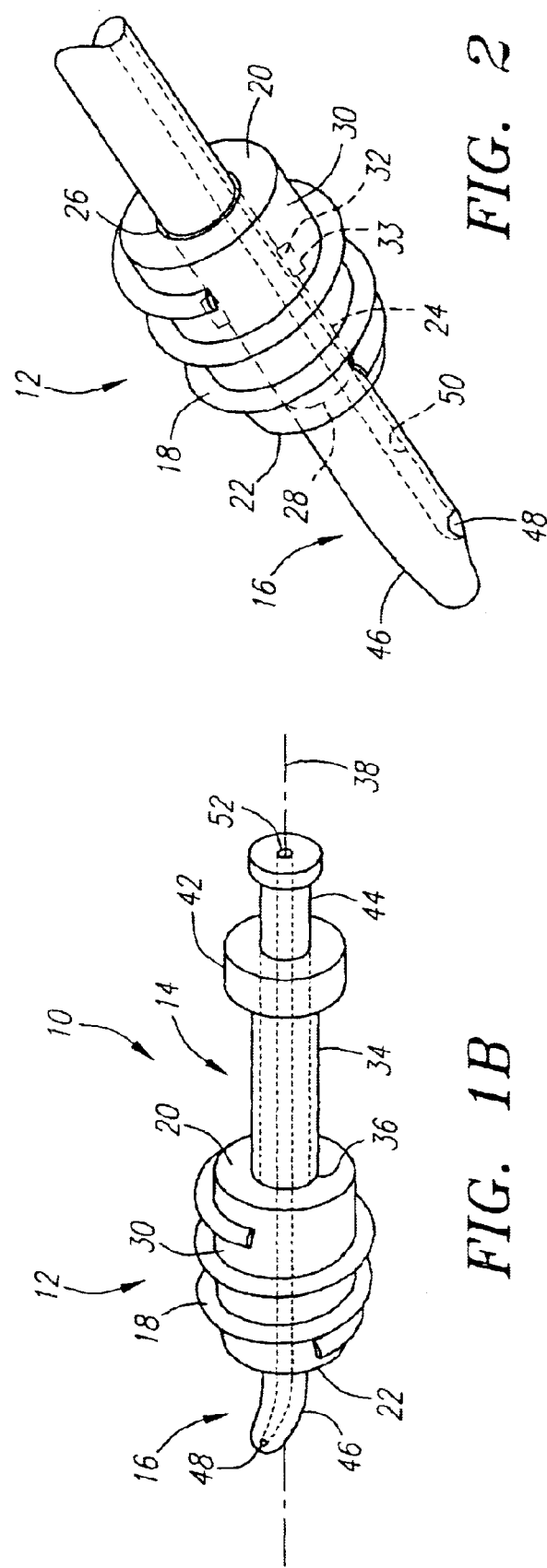

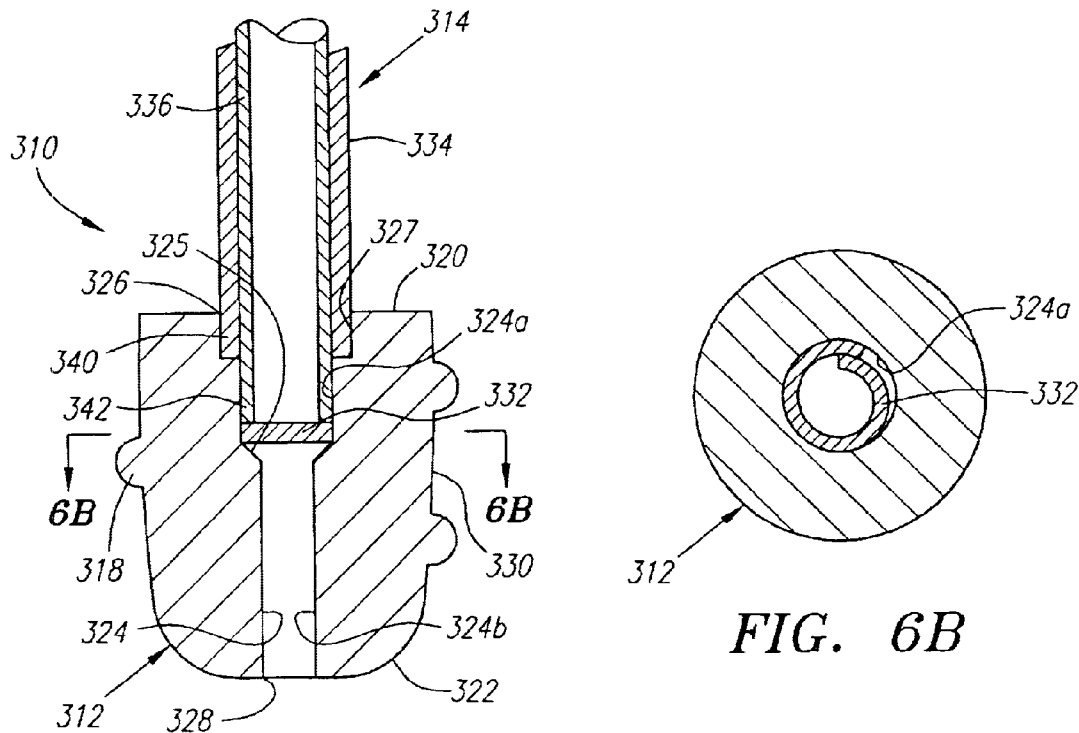
FIG. 6A
FIG. 6B
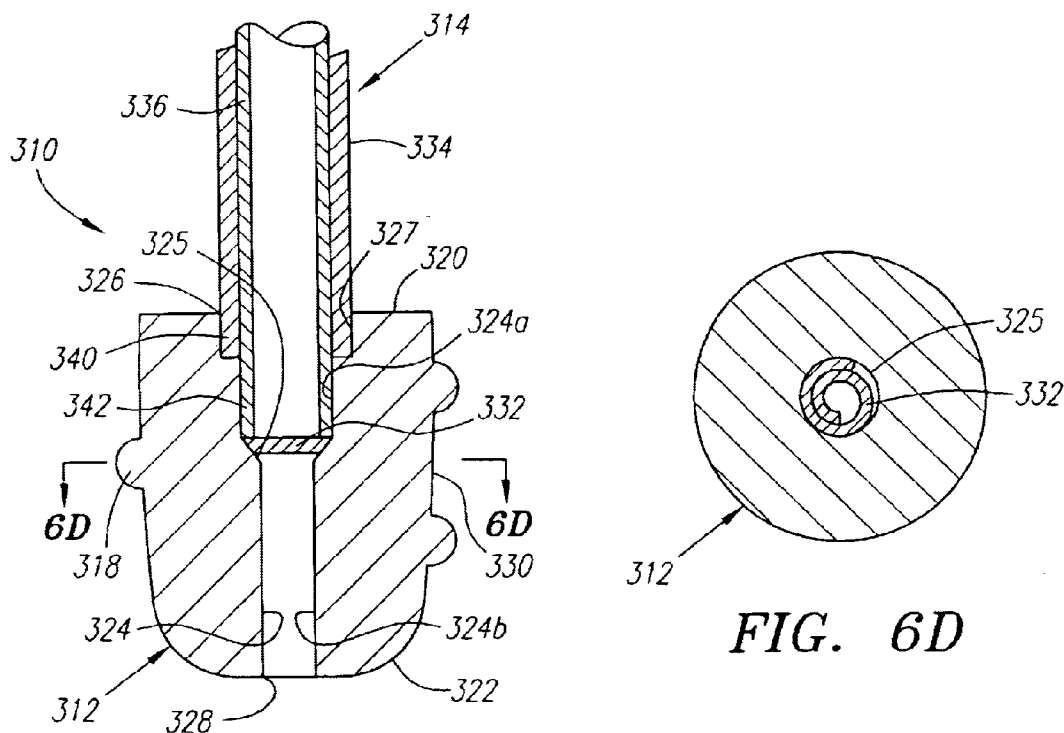
FIG. 6C
FIG. 6D

APPARATUS AND METHODS FOR SEALING VASCULAR PUNCTURES

This application is a continuation-in-part of application Ser. No. 09/738,431, filed Dec. 14, 2000, the disclosure of which is expressly incorporated herein by reference.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Accordingly, devices for sealing punctures or other passages through tissue, e.g., an opening into a blood vessel, would be considered useful.

SUMMARY OF THE INVENTION

The present invention is directed to apparatus and methods for sealing or closing passages through tissue, such as punctures communicating with blood vessels or other body lumens.

In accordance with one aspect of the present invention, a device for sealing a passage through tissue is provided that includes a body, e.g., formed from bioabsorbable material, including a proximal end, a distal end, and a helical thread on an outer surface extending at least partially between the proximal and distal ends. The body includes a lumen extending between the proximal end and a distal inlet port. A sealing member is disposed within the lumen that is expandable for substantially sealing the lumen from fluid flow therethrough.

In a first preferred embodiment, the sealing member includes a material that is expandable when exposed to fluid to substantially seal the lumen, such as a foam and/or a bioabsorbable material. The sealing member may be a valve or other device that is biased towards a first configuration for substantially sealing the lumen from fluid flow therethrough, and is movable to a second configuration for accommodating introduction of one or more devices through the lumen.

In a second preferred embodiment, the lumen includes a tapered portion that tapers in cross-section, and the sealing member is a generally annular-shaped member disposed adjacent a wide end of the tapered portion of the lumen. The sealing member is movable into the tapered portion for substantially sealing the lumen from fluid flow therethrough.

In accordance with another aspect of the present invention, an apparatus is provided for sealing a passage through tissue that includes a handle device or other elongate member and a plug member. The elongate member has a proximal end, a distal end, and a lumen extending between the proximal and distal ends. The plug member is disposed on the distal end of the elongate member, and includes a helical thread on its outer surface and a distal port therein in communication with the lumen.

Preferably, the plug member includes a passage therein extending between the distal port and the lumen. A sealing member may be disposed in the passage for substantially sealing the passage from fluid flow therethrough, such as that described above. In one embodiment, the passage and lumen define a bleed back lumen for determining the location of the plug member relative to a blood vessel or other body lumen.

In another embodiment, an obturator or other elongate member is insertable through the lumen such that a distal end of the obturator is disposed beyond the distal end of the plug member. The obturator may include a location indicator for identifying when the distal end of the plug member is disposed adjacent a body lumen. The location indicator may include a bleed back lumen in the obturator and a bleed back port on its distal tip, the bleed back port being in communication with the bleed back lumen. Alternatively, the location identifier may include an expandable member on a distal tip of the obturator, the expandable member being expandable when the distal tip is disposed within a body lumen for providing tactile feedback of a location of the distal end of the plug member with respect to the body lumen.

Preferably, the plug member is releasable from the elongate member. The elongate member may include an actuator for releasing the plug member from the distal end of the elongate member. Preferably, cooperating connectors are provided on the distal end of the elongate member and on the plug member for releasably securing the plug member to the distal end of the elongate member.

In accordance with yet another aspect of the present invention, a method is provided for sealing a passage through tissue communicating with a body lumen using an apparatus, such as that described above. Generally, the apparatus includes an elongate member, and a plug member disposed on a distal end of the elongate member. The plug member includes an outer surface including a helical thread, and a bleed back indicator associated with a distal end of the plug member.

The plug member is inserted into the passage until the helical thread begins to enter the passage. The elongate member may be rotated in a first direction, thereby threading the plug member into the passage until the bleed back indicator enters the body lumen, whereupon fluid from the body lumen may enter the bleed back indicator to identify the location of the body lumen with respect to the plug member. If desired, rotation of the elongate member may be reversed, thereby withdrawing the plug member a predetermined distance relative to the body lumen.

Thereafter, the plug member may be released from the elongate member within the passage. Preferably, the plug member is formed from bioabsorbable material, and the plug member is left within the passage until it is absorbed by the tissue.

In a preferred embodiment, the elongate member includes a lumen extending from its proximal end through the plug member, and the bleed back indicator includes a bleed back port in the plug member, the bleed back port being in communication with the lumen. Alternatively, an obturator may be inserted through the lumen until a distal end of the obturator extends distally beyond the plug member, and the bleed back indicator may include a bleed back lumen in the obturator.

A sealing member may be provided in a lumen of the plug member for sealing the lumen, and consequently the bleed back port, from fluid flow therethrough. The sealing member may be an expandable material that expands when exposed to fluid. Alternatively, the sealing member may be a generally annular shaped element that may be disposed adjacent a wide end of a tapered portion of the lumen. The annular-shaped may be moved or otherwise wedged into the tapered portion for substantially sealing the lumen.

Other objects and features of the present invention will become apparent from consideration of the following description taken in conjunction with the accompanying drawings.

BRIEF DESCRIPTION OF THE DRAWINGS

FIG. 1A is an exploded perspective view of a first preferred embodiment of an apparatus for sealing a passage through tissue, in accordance with the present invention.

FIG. 1B is a perspective view of the assembled apparatus of FIG. 1A.

FIG. 2 is a detail of a distal end of the apparatus of FIGS. 1A and 1B.

FIG. 6A is a cross-sectional side view of a fourth embodiment of an apparatus for sealing a passage through tissue, including a plug member with a sealing member within its lumen, in accordance with the present invention.

FIG. 6B is a cross-sectional detail of the plug member of FIG. 6A, taken along line 6B–6B, showing the sealing member in an open configuration.

FIG. 6C is a cross-sectional side view of the apparatus of FIG. 6A, with the sealing member wedged into a tapered portion of the lumen.

FIG. 6D is a cross-sectional detail of the plug member of FIG. 6C, taken along line 6D—6D, showing the sealing member wedged into a closed configuration.

DETAILED DESCRIPTION OF THE PREFERRED EMBODIMENTS

Figure 3A:
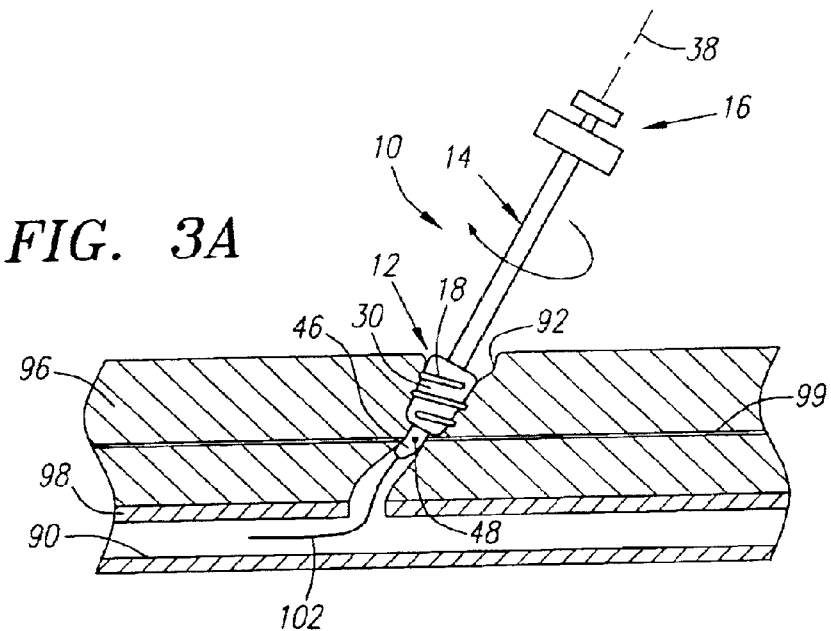
FIGS. 3A–3D are cross-sectional views showing a plug member on the apparatus of FIGS. 1A and 1B being used to seal an opening in a wall of a blood vessel.

Turning now to the drawings, FIGS. 1A, 1B, and 2 show a first preferred embodiment of an apparatus 10 for sealing a passage through tissue, in accordance with the present invention. Generally, the apparatus 10 includes a plug member 12, an elongate shaft or handle device 14, and an obturator 16.

The plug member 12 is a substantially rigid body, preferably having a generally cylindrical shape, including a proximal end 20, a distal end 22, and an outer surface 30. The plug member 12 includes a lumen 24 that extends between a proximal opening 26 and a distal opening or port 28.

The plug member 12 may be formed from a biocompatible material, e.g., a plastic, such as polyethylene or polyester. Preferably, the plug member 12 is formed at least partially (and more preferably entirely) from bioabsorbable material, such as collagen, polyglycolic acids (PGA's), polyactides (PLA's), and the like, that may be at least partially absorbed by the patient's body over time. Alternatively, the plug member 12 may be a semi-rigid or flexible body or may have a substantially flexible distal tip (not shown), e.g., to facilitate atraumatic insertion of the plug member 12 into the passage. In addition or alternatively, the plug member 12 may be tapered along its length, and/or the distal end 22 may be rounded to facilitate advancement of the plug member 12 into a passage through tissue.

In a preferred embodiment, the plug member 12 has a length of not more than about ten millimeters (10 mm), and more preferably between about one and ten millimeters (1–10 mm). The plug member 12 also preferably has a diameter of between about one and twenty millimeters (1–20 mm). Preferably, the length and diameter have a ratio that not more than about two-to-one.

The plug member 12 generally includes a helical thread pattern 18, including one or more helical threads, that extend at least partially between its proximal and distal ends 20, 22. Preferably, the thread pattern 18 extends completely to the distal end 22 of the plug member 12, and may be tapered at the distal end 22 to facilitate introduction into a passage through tissue (not shown). The helical thread 18 is preferably substantially rigid and may have a substantially square cross-section to facilitate sealing of a passage into which the plug member 12 is threaded. In a preferred embodiment, the helical thread 18 is integrally formed on the outer surface 30 of the plug member 12. For example, the plug member 12 and thread 18 may be formed by injection molding. Alternatively, the threads may be cut or otherwise formed in the outer surface 30 of the plug member 12.

As best seen in FIG. 2 (in which the handle device 14 has been eliminated for convenience), a sealing member 32 is provided within the lumen 24 for substantially sealing the lumen 24 from fluid flow therethrough. In a preferred embodiment, the sealing member 32 has an annular shape, and is mounted within an annular recess 33 in the lumen 24. The sealing member 32 is preferably formed from a material that expands when exposed to fluids, e.g., an expandable foam. More preferably, the sealing member 32 is also bioabsorbable, similar to the plug member 12 itself. Exemplary materials that may be appropriate for use in the sealing member 32 and/or for the plug member 12 are disclosed in U.S. Pat. No. 6,224,630, the disclosure of which is expressly incorporated herein by reference. Alternatively, the sealing member 32 may be a valve (not shown) that is biased to substantially seal the lumen 24 from fluid flow, but may be opened to facilitate introduction of one or more devices, e.g., the obturator 16 therethrough, as described further below.

In an alternative embodiment, the plug member 12 may include a cavity (not shown) in the distal end 22. A material (also not shown) may be provided in the cavity, such as extra-cellular matrix material, e.g., intestinal, stomach, or bladder submucosa, collagen, an infection-resistant material, and the like, that may promote hemostasis and/or healing of the tissue. Alternatively, such material may be otherwise detachably secured to the distal end 22 of the plug member 12, either within a cavity or across the distal end 22 without a cavity. For example, the material may be secured using a biodegradable adhesive or a mechanical fastener, such as one or more clips (not shown).

Returning to FIGS. 1A and 1B, the handle device 14 has a proximal end 34 and a distal end 36, and defines a longitudinal axis 38 that extends between the proximal and distal ends 34, 36. A lumen 40 also extends between the proximal and distal ends 34, 36, e.g., for accommodating insertion of the obturator 16 therethrough. A handle 42 may be provided on the proximal end 34 of the handle device 14 for facilitating manipulation of the apparatus 10, e.g., to facilitate rotation of the apparatus 10 into a passage, as described below.

Preferably, the handle device 14 is a substantially rigid tubular member, formed from a biocompatible material, e.g., plastic, such as polyethylene or polyester, or metal, such as stainless steel. The handle device 14 preferably has a cross-section that is substantially smaller than a cross-section of the plug member 12, e.g., to minimize dilation of a passage into which the apparatus 10 is inserted.

At least one of the plug member 12 and the distal end 36 of the handle device 14 include a connector. Preferably, the plug member 12 and the distal end 36 of the handle device 14 include cooperating connectors (not shown) for releasably securing the plug member 12 to the handle device 14, as described in application Ser. No. 09/738,431, incorporated above. Preferably, the cooperating connectors substantially couple the plug member 12 to the handle device 14 such that the plug member 12 cannot move independently of the handle device 14, e.g., such that the plug member 12 may be rotated only by rotating the handle device 14.

For example, the plug member 12 may include a recess (not shown) in its proximal end 20 and the handle device 14 may include a mechanism, e.g., a frame and/or radially projecting fingers (not shown), for frictionally engaging the wall of the recess. Alternatively, the recess may include slots for positively receiving the mechanism on the handle device 14. In a further alternative, the plug member 12 may include a hub (not shown) extending from its proximal end 20 and the handle device 14 may include a mechanism for detachable securing the hub to the handle device 14.

Preferably, the handle 42 includes an actuator (not shown) that may be activated to release the connectors securing the plug member 12 to the handle device 14. For example, the actuator may include a button coupled to a control rod or wire (not shown) that extends through the handle device 14 to its distal end 36. Upon depression of the button, the control rod may be moved, thereby disengaging the connector on the handle device 14 from the mating connector on the plug member 12. In another alternative, the distal end 36 of the handle device 14 and the plug member 12 may include mating threads (not shown) so that the handle device 14 may be rotated with respect to the plug member 12 to release the plug member 12. In this embodiment, the mating threads should wind helically in the same direction as the thread pattern 18 on the plug member 12 to ensure that the plug member 12 is not released prematurely from the handle device 14.

The obturator 16 is an elongate member, preferably having a proximal end 44 and a substantially atraumatic and/or flexible distal tip 46. An inlet or bleed back port 48 is provided on the distal tip 46, and a bleed back lumen 50 extends from the inlet port 48 to the proximal end 44. The proximal end 44 may include an outlet port 52, which may include any conventional structure for detected or observing fluid passing from the back bleed lumen 50.

The obturator 16 has a size and shape for insertion through the lumen 40 of the handle device 14 and through the lumen 24 of the plug member 12. Once the obturator 16 is fully received through the handle device 14, the distal tip 46 of the obturator 16 may extend beyond the distal end 22 of the plug member 12, as shown in FIG. 1B. The obturator 16 and the handle device 14 may include cooperating detents (not shown) for securing the obturator 16 once it is fully received through the handle device 14 and plug member 12. The detents may substantially permanently or releasably couple the obturator 16 to the handle device 14.

In alternative embodiments, an expandable member (not shown) may be provided on or adjacent the distal tip 46 of the obturator 16, in addition to or instead of the bleed back port and lumen 48, 50. The expandable member may be expandable, e.g., when the distal tip is disposed within a body lumen, for providing tactile feedback of a location of the distal end of the plug member with respect to the body lumen. The expandable member may be a balloon, one or more expandable wings, such as those disclosed in application Ser. No. 09/732,835, filed Dec. 7, 2000, or a helical tether device, such as that disclosed in application Ser. No. 10/006,400, entitled "Apparatus and Methods for Providing Tactile Feedback to Position a Closure Device," filed on the same day as the present application (attorney docket no. 260/100). The disclosures of these applications and any other references cited therein are expressly incorporated herein by reference.

Turning to FIGS. 3A–3D, during use, the apparatus 10 may be used to seal and/or close a passage through tissue 96, such as a puncture 92 communicating with a blood vessel 90 or other body lumen. The puncture 92 may be used to provide percutaneous access to the vessel 90. For example, the puncture 92 may facilitate performing an endovascular procedure within a patient's vasculature, such as angioplasty, stenting, atherectomy, and the like, or may otherwise provide access via the vessel 90 to a region within the patient's body.

Upon completion of the procedure, any instruments, such as an introducer sheath (not shown), may be removed from the vessel 90 and puncture 92. If a guidewire 102 is used during the procedure, the guidewire 102 may be removed before delivering the plug member 12, or preferably, the guidewire 102 may be used to guide the plug member 12 into position, as described below.

Initially, the apparatus 10 is assembled as shown in FIG. 1B, i.e., the plug member 12 is connected to the handle device 14, and the obturator 16 is inserted through the handle device 14 and plug member 12. The apparatus 10 may then be introduced into the puncture 92, for example, initially by inserting the distal tip 46 of the obturator 16 into the puncture 92. If the guidewire 102 is in place, generally as shown, the guidewire 102 may be backloaded into a guidewire lumen (not shown) in the obturator 16 in a conventional manner before inserting the distal tip 46 into the puncture 92.

As the obturator 16 is advanced into the puncture 92 (e.g., over the guidewire 102), the plug member 12 is inserted into the puncture 92, as shown in FIG. 3A. Because of the thread pattern 18, the handle device 14 is then rotated in a first direction to thread the plug member 12 into the puncture 92. Consequently, the outer surface 30 and thread pattern 18 engage tissue 96 surrounding the puncture 92, thereby substantially sealing the puncture 92 from fluids, such as blood, within the vessel 90. The apparatus 10 may then be rotated in a first direction about its longitudinal axis 38 to thread the plug member 12 substantially atraumatically deeper into the puncture 92.

Figure 3B:
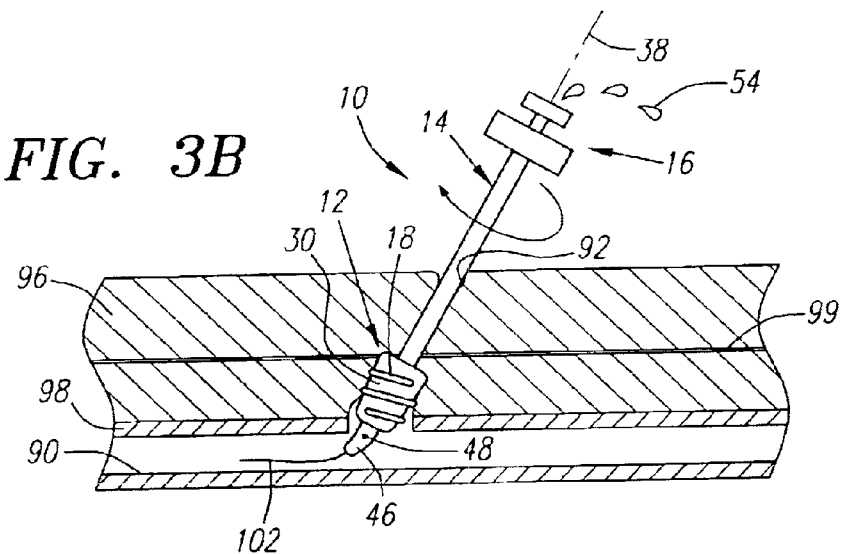

Turning to FIG. 3B, as the plug member 12 is advanced, the thread pattern 18 may facilitate advancement of the plug member 12 through layers of tissue towards the vessel 90. For example, the tissue 96 may include one or more intermediate layers of fascia 99 or other tissue structures disposed between layers of fat. The fascia layer 99 may be relatively thin, yet resilient and tough, and therefore it may be difficult to advance a device axially through the layer 99 without deflecting the layer 99 towards the vessel 90. Because of the thread pattern 18, a plug member 12 in accordance with the present invention may be threaded or screwed through the fascia layer 99 towards the vessel 90. This may substantially reduce the risk of the fascia layer 99 being deflected towards the vessel 90 as the plug member 12 is advanced towards the vessel 90, thereby minimize deflection of the plug member 12 away from the vessel 90 once released within puncture 92 that may otherwise occur if the fascia layer 99 is compressed towards the vessel 90.

When the plug member 12 is advanced into the puncture 92, the distal tip 46 of the obturator 16 eventually passes through the wall 98 of the vessel 90, whereupon the bleed back port 48 becomes exposed to fluid, i.e., blood, within the vessel 90. Because of internal blood pressure, the fluid enters the bleed back port 48, passes through the bleed back lumen 50 (not shown in FIGS. 3A–3D), and exits the outlet port 52 (as represented by drops 54), thereby providing a visual indication that the vessel 90 has been attained. Because of the relative lengths of the plug member 12, the handle device 14, and the obturator 16, this visual indication provides feedback on the location of the distal end 22 of the plug member 12 relative to the vessel 90, as will be appreciated by those skilled in the art. The relative lengths may be predetermined such that the plug member 12 is at a preferred deployment depth when the bleed back indication is observed. For example, the deployment depth may place the plug member 12 in close proximity to the vessel 90, e.g., without exposing the distal end 22 within the vessel 90.

Figure 3C:
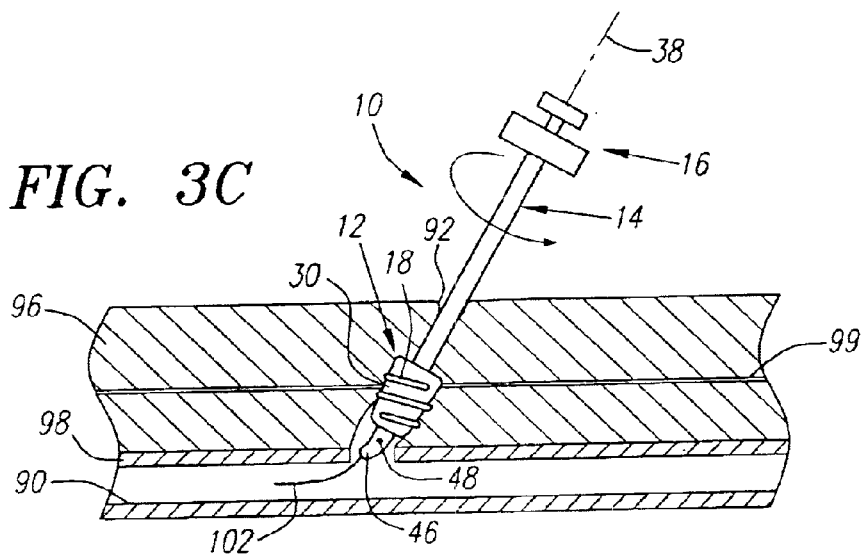

Preferably, the relative lengths may be such that the apparatus 10 needs to be counter-rotated to attain the preferred deployment depth. For example, bleed back may occur when the plug member 12 is within or in close proximity to the vessel 90, as shown in FIG. 3B. Rotation of the apparatus 10 may then be reversed, i.e., in a second direction opposite the first direction, to withdraw the plug member 12 a predetermined distance relative to the vessel 90, as shown in FIG. 3C. Because of the known pitch of the thread pattern 18, the distance that the plug member 12 is moved relative to the vessel 90 may be related directly to the number of rotations and/or partial rotations that the apparatus 10 is counter-rotated.

Once the desired deployment location is attained, the plug member 12 may be released from the handle device 14. The obturator 16 may be withdrawn from the plug member 12 and handle device 14 either before or after releasing the plug member 12. The sealing member 32 (not shown, see FIG. 2) preferably substantially seals the lumen (not shown, see FIG. 2) within the plug member 12 to prevent fluid within the vessel 90 from passing therethrough to leak from the puncture.

Preferably, as explained above, the sealing member 32 is a material that expands when exposed to fluid. For example, as the obturator 16 is withdrawn, fluid, e.g., blood, may flow proximally through the lumen 24 in the plug member 12, e.g., until it encounters the sealing member 32. Although a relatively small amount of fluid may pass beyond the sealing member 32, the sealing member 32 may expand substantially due to the fluid contact until it substantially seals the lumen. Alternatively, the sealing member 32 may be a valve that may open to accommodate the obturator 16, but may automatically close upon withdrawal of the obturator 16.

Figure 3D:
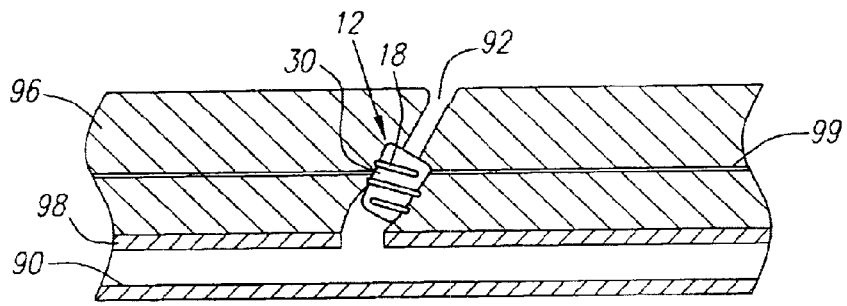

Finally, as shown in FIG. 3D, the handle device 14 and the guidewire 102 (if still in place) may be withdrawn, leaving the plug member 12 in place to substantially seal the puncture 92. If the plug member 12 is bioabsorbable, it may remain within the puncture 92 as the tissue heals, thereby allowing the wall 98 of the vessel 90 and tissue 96 surrounding the passage 92 to at least partially heal before the plug member 12 is absorbed. Alternatively, the plug member 12 may be retrieved once the tissue between the plug member 12 and the vessel 90 has substantially healed, as described in the application incorporated above.

Figure 4A:
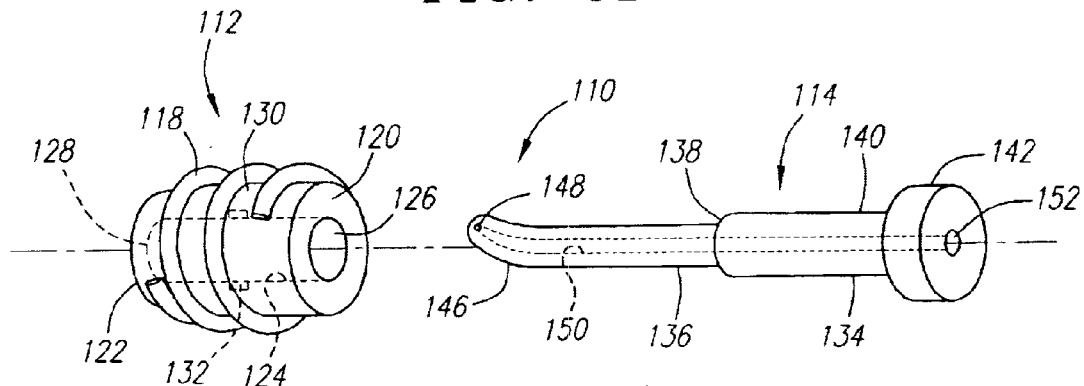
FIG. 4A is an exploded perspective view of a second preferred embodiment of an apparatus for sealing a passage through tissue, in accordance with the present invention.
Figure 4B:
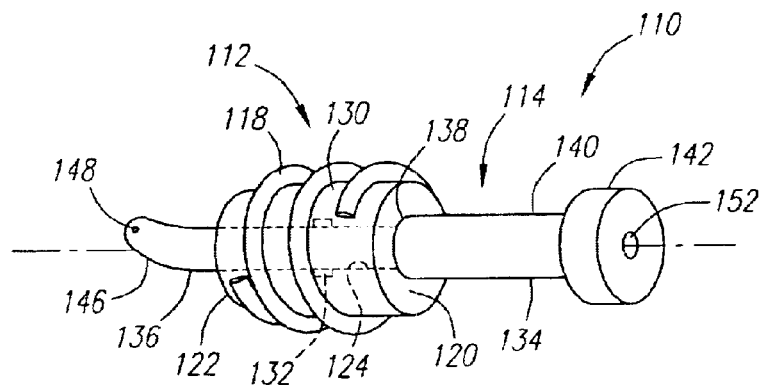
FIG. 4B is a perspective view of the assembled apparatus of FIG. 4A.

Turning to FIGS. 4A and 4B, another embodiment of an apparatus 110 is shown that includes a plug member 112 and a handle device 114. The plug member 112 includes a body, preferably formed from bioabsorbable material, including a proximal end 120 and a distal end 122. A helical thread pattern 118 extends along an outer surface 130 of the plug member 112 at least partially between the proximal and distal ends, similar to the embodiment described above. In addition, the plug member 112 includes a lumen 124 and a sealing member 132 disposed within the lumen 124, similar to the embodiment described above.

The handle device 114 is an elongate member having an enlarged portion 134 and a reduced portion 136 defining a shoulder 138 therebetween. The enlarged portion 134 may include a handle 142 on the proximal end 140. The reduced portion 136 has a size for insertion through the lumen 124 of the plug member 112 and terminates in a distal tip 146 that may be substantially atraumatic and/or flexible, similar to the obturator distal tip described above. A bleed back port 148 is provided in the distal tip 146 that communicates with a bleed back lumen 150 that extends to an outlet port 152 in the proximal end 140.

As shown in FIG. 4B, the reduced portion 136 may be inserted into the lumen 124 until the distal tip 146 extends beyond the distal end 122 of the plug member 112 and/or the shoulder 138 abuts the proximal end 120 of the plug member 112. Alternatively, the shaft of the handle device 114 may have a substantially uniform cross-section, similar to the reduced portion 134, and a raised portion (not shown) may be provided on the shaft, e.g., an annular ridge against which the plug member 112 may abut. Thus, the shoulder 138 or other raised portion may limit proximal movement of the plug member 112 relative to the handle device 114.

Preferably, the plug member 112 and the handle device 114 include cooperating elements (not shown) for coupling the plug member 112 to the handle device 114, i.e., to prevent rotation of the plug member 112 relative to the handle device 114. For example, all or a portion of the reduced portion 136 of the handle device 114 may have a noncircular cross-section, and all or a mating portion of the lumen 124 may have a complementary noncircular cross-section. Alternatively, cooperating longitudinal slots and tabs and the like may be provided on the reduced portion 136 and within the lumen 124 of the plug member 114. Thus, when the reduced portion 136 is fully inserted through the lumen 124, rotation of the plug member 112 may be coupled to rotation of the handle device 114. In a further alternative, the plug member 112 and the handle device 114 may include connectors that may releasably couple the plug member 112 to the handle device 114, similar to the embodiment described above.

The apparatus 110 may be used to seal and/or close a passage through tissue, such as a puncture communicating with a blood vessel or other body lumen (not shown), similar to the embodiment described above. Upon completion of a procedure accessed via the puncture, any instruments may be removed from the vessel and puncture, although a guidewire (not shown) may remain, similar to the embodiment described above. The apparatus 110 may be assembled as shown in FIG. 4B, i.e., with reduced portion 134 of the handle device 114 fully inserted into the plug member 112. The distal tip 146 may be inserted into the puncture, e.g., over a guidewire (not shown) if still in place within the puncture, until the plug member 112 is inserted into the puncture 92.

The apparatus 110 may then be rotated to thread the plug member 112 into the puncture such that the outer surface 130 and thread pattern 118 engage tissue surrounding the puncture to substantially seal the puncture. When the distal tip 146 enters the vessel, the bleed back port 148 becomes exposed to blood within the vessel. Because of internal blood pressure, fluid within the vessel enters the port 148, passes through the bleed back lumen 150, and exits the outlet port 152, thereby providing a visual indication that the vessel has been attained.

If desired, rotation of the apparatus 110 may then be reversed to withdraw the plug member 112 a predetermined distance relative to the vessel. The plug member 112 may then be released from the handle device 114. The handle device 114 may then be withdrawn from the plug member 112 (and the guidewire, if still present). Preferably, the reduced portion 134 of the handle device 114 may simply be withdrawn from within the lumen 124, without requiring disengagement of connectors, which may simplify construction of the handle device 114 compared to the embodiment described above. As the reduced portion 134 is withdrawn from the lumen 124, the sealing member 132 becomes exposed to fluid passing through the lumen 124. Preferably, as explained above, the sealing member 132 expands when exposed to the fluid to substantially seal the lumen 124 from subsequent fluid flow. Alternatively, the sealing member 132 may be a valve or an element that may controllably opened or closed (not shown).

Figure 5:
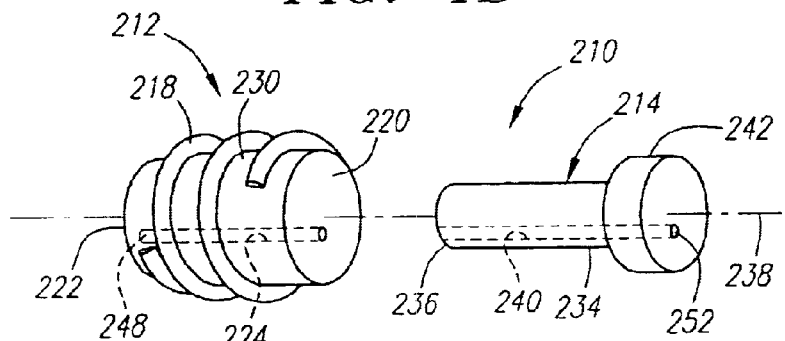
FIG. 5 is a side view of a third preferred embodiment of an apparatus for sealing a passage through tissue, in accordance with the present invention.

Turning to FIG. 5, yet another embodiment of an apparatus 210 is shown that includes a plug member 212 and a handle device 214. The plug member 212 includes a body, preferably formed from bioabsorbable material, including a proximal end 220, a distal end 222, and a helical thread pattern 218 that extends along an outer surface 230 at least partially between the proximal and distal ends 220, 222, similar to the embodiment described above. In addition, the plug member 212 includes a lumen 224 including an inlet or bleed back port 248 and a sealing member (not shown) disposed within the lumen 224. Alternatively, the lumen 224 may have a sufficiently small cross-section that a sealing member may not be necessary.

The handle device 214 has a proximal end 234 and a distal end 236, and defines a longitudinal axis 238 that extends between the proximal and distal ends 234, 236. A lumen 240 also extends between the proximal and distal ends 234, 236. A handle 242 may be provided on the proximal end 234 of the handle device 214 for facilitating manipulation of the apparatus 210, e.g., to facilitate rotation of the apparatus 210 into a passage, similar to the embodiments described above. An outlet port 252 is provided on the proximal end 234, e.g., in the handle 242, that communicates with the lumen 240. Preferably, the handle device 214 is a substantially rigid elongate shaft formed from biocompatible material. The handle device 214 preferably has a cross-section that is substantially smaller than a cross-section of the plug member 212, similar to the embodiments described above.

The plug member 212 and the distal end 236 of the handle device 214 generally include cooperating connectors (not shown) for releasably securing the plug member 212 to the handle device 214, similar to the first embodiment described above. Preferably, the cooperating connectors substantially couple the plug member 212 to the handle device 214 such that the plug member 212 cannot move independently of the handle device 214, e.g., such that the plug member 212 may be rotated only by rotating the handle device 214.

Preferably, the handle 242 includes an actuator (not shown) that may be activated to release the connectors securing the plug member 212 to the handle device 214. For example, the actuator may include a button coupled to a control rod or wire (not shown) that extends through the handle device 214 to its distal end 236. Upon depression of the button, the control rod may be moved, thereby disengaging the connector on the handle device 214 from the mating connector on the plug member 212.

Before use, the plug member 212 may be coupled to the distal end 236 of the handle device 114. Once the plug member 212 is attached to the distal end 236, the lumen 224 in the plug member 212 communicates with the lumen 240 in the handle device 214.

The apparatus 210 may be used to seal and/or close a passage through tissue, similar to the embodiments described above. After performing a procedure accessed via the puncture, the distal end 236 of the plug member 212 may be inserted into the puncture. The apparatus 210 may then be rotated to thread the plug member 212 deeper into the puncture. When the distal end 236 of the plug member 212 enters the vessel, the bleed back port 248 becomes exposed to blood within the vessel, causing fluid within the vessel to enter the port 248, pass through the lumens 224, 240, and exit the outlet port 252, thereby providing a visual indication that the vessel has been attained.

If desired, rotation of the apparatus 210 may then be reversed to withdraw the plug member 212 a predetermined distance relative to the vessel. The plug member 212 may then be released from the handle device 214. The handle device 214 may then be withdrawn, leaving the plug member 212 in place to substantially seal the puncture.

If the plug member 212 includes a sealing member, the sealing member is exposed to fluid passing through the lumen 224, causing the sealing member to expand when exposed to fluid contact to substantially seal the lumen 224 from subsequent fluid flow. Alternatively, if no sealing member is provided, the lumen may be sufficiently small such that hemostasis may still occur. The lumen 224 may begin to seal on its own or, if necessary, external pressure may be applied to the puncture to promote hemostasis.

Turning to FIGS. 6A–6D, yet another embodiment of an apparatus 310 is shown that includes a plug member 312 and a handle device 314. The plug member 312 includes a body, preferably formed from bioabsorbable material, including a proximal end 320 and a distal end 322. A helical thread pattern 318 extends along an outer surface 330 of the plug member 312 at least partially between the proximal and distal ends 320, 322, similar to the embodiments described above.

In addition, the plug member 312 includes a lumen 324 that extends between a proximal opening 326 and a distal opening 328 generally parallel to a longitudinal axis 338. The lumen 324 includes a tapered portion 325 that tapers towards the distal end 322. The lumen may include a proximal portion 324a and a distal portion 324b on either side of the tapered portion 325 that may be substantially uniform in cross-section. Thus, the distal opening 328 may be substantially smaller than the proximal opening 326, e.g., corresponding to the respective portions of the tapered portion 325. In addition, the plug member 312 may include an annular recess 327 disposed concentrically around the proximal opening 326.

A sealing member 332 is disposed in an open position adjacent the wide end of the tapered portion 325 of the lumen 324. The sealing member 332 is a generally annular-shaped member, preferably a coil of material including one or more overlapping layers, which may be formed from a biocompatible, and preferably a bioabsorbable material, similar to the plug member 312 itself. Alternatively, the sealing member 332 may be an enclosed ring that may be formed from semi-rigid or flexible material. In its open position, the proximal portion 324a of the lumen 324 is substantially open, i.e., the sealing member 332 does not generally obstruct the lumen 324. The sealing member 332 is movable distally into the tapered portion 325 to become compressed or wedged therein, thereby defining a closed position for substantially sealing the lumen 324 from fluid flow therethrough.

The handle device 314 includes an outer carrier tube 334, and an inner delivery tube 336, the inner tube 336 being coaxially and/or slidably disposed within the outer tube 334. The handle device 314 may include a handle and/or actuator (not shown) on a proximal end of the handle device 314 for manipulating the handle device 314 and/or for controlling movement of the inner tube 336 relative to the outer tube 334. A distal end 340 of the outer tube 334 may be received in the annular recess 327 to couple the plug member 312 to the handle device 314. The distal end 340 may frictionally engage a wall of the recess 327, e.g., providing a desired resistance to removing the distal end 340 from the recess 327. In addition or alternatively, the distal end 340 and/or the plug member 312 may include one or more connectors (not shown), similar to the embodiments described above.

A distal end 342 of the inner tube 336 preferably has a size for being slidably received into the proximal portion 324a of the lumen 324. Preferably, when the distal end 340 of the outer tube 334 is disposed within the recess 327, the distal end 342 of the inner tube 336 extends into the proximal portion 324a of the lumen 324 in close proximity, e.g., contacting, the sealing member 332. The inner tube 336 preferably includes a lumen 344 that communicates with the lumen 324, more preferably the distal portion 324b of the lumen 324. Thus, the lumens 344, 324 may provide a bleed back lumen, similar to the embodiments described above.

During use, the apparatus 310 is assembled by inserting the distal end 340 of the outer tube 334 into the recess 327 and the distal end 342 of the inner tube 336 in the proximal portion 324a of the lumen 324, as shown in FIGS. 6A and 6B. The plug member 312 is inserted into a passage communicating with a blood vessel or other body lumen (not shown), and threaded through the tissue towards the vessel, e.g., by rotating the apparatus 310 in a first direction. When the distal end 322 of the plug member 312 enters the vessel, fluid may flow into the distal opening 328, through the lumens 324, 344 to a proximal outlet port or other bleed back indicator (not shown) on the handle device 314. If desired, the apparatus 310 may be counter-rotated in a second direction until the plug member 312 is disposed at a desired location within the passage.

The inner tube 336 may then be advanced distally relative to the outer tube 334, thereby engaging the sealing member 332 and forcing it distally into the tapered portion 325 of the lumen 324. Because of its inherent flexibility and/or because of its coil shape, the sealing member 325 may compress and/or otherwise become wedged into the tapered portion 325, thereby substantially sealing the lumen 324 from fluid flow therethrough, as shown in FIGS. 6C and 6D. The plug member 312 may then be released from the handle device 314, e.g., by withdrawing the outer tube 336 (without rotating it to unthread the plug member 312) and/or by releasing connectors securing the plug member 312 to the distal end 340 of the outer tube 334. The handle device 314 may then be withdrawn form the passage, leaving the plug member 312 in place, similar to the embodiments described above.

Turning to FIGS. 7A–7D, an apparatus 410 is shown that includes a plug member 412 and an elongate shaft or handle device 414. The plug member 412 may be formed from biocompatible and/or bioabsorbable material, similar to the embodiments described above. The plug member 412 includes a proximal end 420, a distal end 422, and an outer surface 430, and a lumen 424 that extends between the proximal and distal ends 420, 422. The plug member 412 generally includes a helical thread pattern 418, including one or more helical threads, that extend at least partially between its proximal and distal ends 420, 422. A sealing member 432 may be provided within the lumen 424, such as those described above.

The handle device 414 has a proximal end 434 and a distal end 436, and defines a longitudinal axis 438 that extends between the proximal and distal ends 434, 436. In one embodiment, the handle device 414 is tubular, and includes a lumen 440 extending between the proximal and distal ends 434, 436, the lumen 440 communicating with the lumen 424 when the plug member 412 is attached to the distal end 434 of the handle device 414. A handle 442 may be provided on the proximal end 434 of the handle device 414 for facilitating manipulation of the apparatus 410, e.g., to facilitate rotation of the apparatus 410 into a passage.

The handle device 414 may be have a cross-section that is substantially smaller than a cross-section of the plug member 412, e.g., to minimize dilation of a passage into which the apparatus 410 is inserted. The plug member 412 and/or the distal end 436 of the handle device 414 may include cooperating connectors (not shown) for releasably securing the plug member 412 to the handle device 414, as described above. Preferably, the handle 442 includes an actuator (also not shown) that may be activated to release the connectors securing the plug member 412 to the handle device 414. Alternatively, the handle device 414 may have a cross-section defining a portion of a circle, e.g., a "C" shape, or may include one or more elongate shafts (not shown) that releasably connect to the plug member 412.

In addition, the plug member 412 and the handle device 414 include a bleed back device for providing a visual indication when the distal end 422 of the plug member 412 is disposed within a blood vessel 90 or other body lumen. For example, as shown, the handle device 414 may include a bleed back lumen 452 that extends between the proximal and distal ends 434, 436. An outlet port 45, a transparent tube (not shown) or other device may be provided on the proximal end 434 of the handle device 414 that communicates with the bleed back lumen 452. The plug member 412 may include a bleed back port 454 that extends from the distal end 422 to the bleed back lumen 452. For example, the bleed back port 454 may be a separate lumen (not shown) extending between the proximal and distal ends 420, 422 of the plug member 412.

Alternatively, the bleed back port 454 may be a groove extending along the lumen 424 of the plug member 412, as shown in FIGS. 7B–7E. In addition or alternatively, the bleed back lumen 452 in the handle device 414 may be a groove (not shown) extending along the lumen 440 between the proximal and distal ends 434, 436 of the handle device 414. The groove(s) may define a substantially enclosed passage when the apparatus 410 is received over an introducer sheath 416 or other elongate member.

The apparatus 410 may be used in conjunction with an introducer sheath 416 or other elongate member, having a proximal end 444 and a distal end 446. The sheath 416 may include a tapered and/or substantially atraumatic distal end 446 having a size for insertion through a puncture into a body lumen 90. The sheath 416 may include a lumen 450 that extends between the proximal and distal ends 444, 446, the lumen 450 having a size to accommodate insertion of one or more devices therethrough. The sheath 416 may include a seal (not shown), e.g., in the lumen 450 adjacent the proximal end 444 to substantially seal the lumen 450, yet accommodate devices (not shown) therethrough.

The apparatus 410 may be attachable to the sheath 416 at any time during a procedure, e.g., such that the plug member 412 and handle device 414 may slide along the sheath 416. Alternatively, the apparatus 410 may be substantially permanently, but slidably, attached to the sheath 416.

Figure 7A:
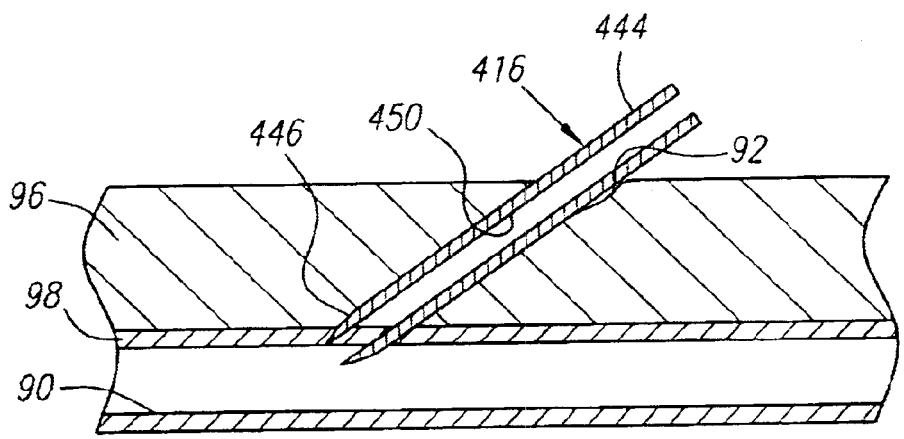
FIGS. 7A–7F are cross-sectional views showing an apparatus and method for delivering a plug member to seal a puncture communicating with a blood vessel.

With particular reference to FIG. 7A, initially, the sheath 416 may be introduced into a puncture or other passage 92 communicating with a blood vessel or other body lumen 90. The distal end 446 may be introduced over a guidewire, a trocar, and/or a dilator (all not shown) until the distal end 446 is disposed in or adjacent to the vessel 90, as is well known to those skilled in the art. One or more instruments or devices (not shown) may be advanced through the lumen 450 into the vessel 90 to perform a procedure at a location within the patient's body accessed by the vessel 90. For example, an endovascular procedure may be performed within a patient's vasculature, such as angioplasty, stenting, atherectomy, and the like.

Figure 7B:
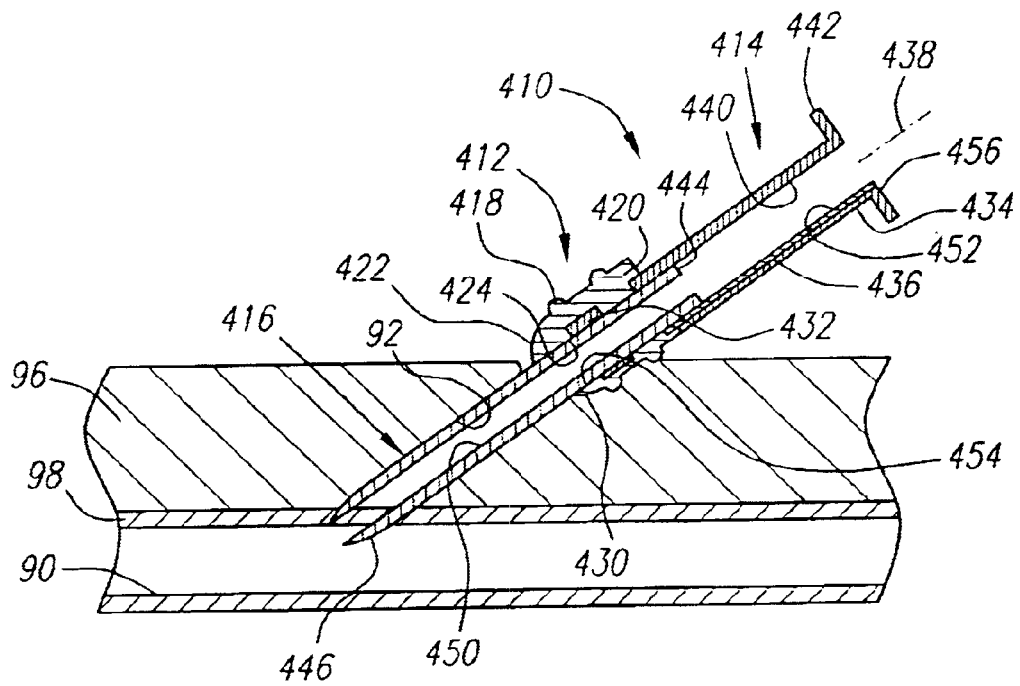

As shown in FIG. 7B, upon completing the procedure, any devices may be removed from the lumen 450, and the plug member 412 may be delivered into the passage 92 using the apparatus 410. With the apparatus 410 assembled, as shown, the apparatus 410 may be introduced into the passage 92 over the sheath 416, i.e., by inserting the proximal end 444 of the sheath 416 into the lumen 424 in the plug member 412 and through the lumen 440 in the handle device 414.

Figure 7C:
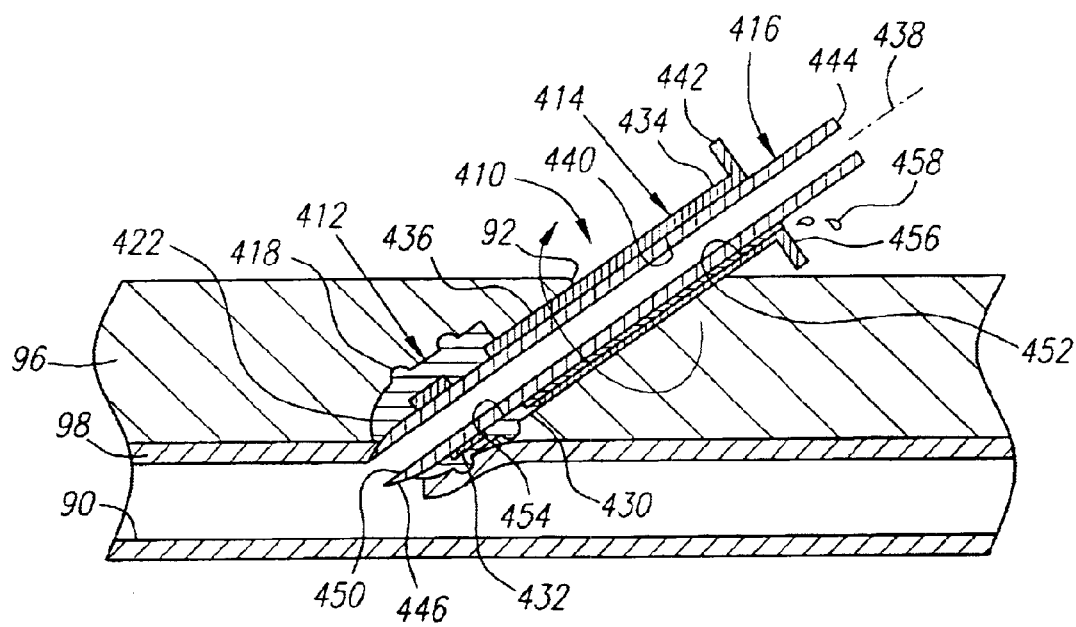

For example, the distal end 422 of the plug member 412 may be inserted into the passage 92 until the thread pattern 418 begins to engage tissue 96 surrounding the passage 92. Then, as best seen in FIG. 7C, the handle device 414 may be rotated in a first direction (indicated by exemplary arrow) to thread the plug member 412 into the passage 92 over the sheath 414. Consequently, the outer surface 430 and/or thread pattern 418 of the plug member 412 may substantially engage tissue 96 surrounding the passage 92, thereby substantially sealing the passage 92 from fluids, such as blood, within the vessel 90.

Turning to FIG. 7C, as the plug member 12 is advanced, the distal end 422 of the plug member 412 may eventually pass through the wall 98 of the vessel 90, whereupon the bleed back port 454 may become exposed to fluid, i.e., blood, within the vessel 90. Because of internal blood pressure, the fluid enters the bleed back port 454, passes through the bleed back lumen 452, and exits the outlet port 456 (as represented by drops 458), thereby providing a visual indication that the vessel 90 has been reached.

Figure 7D:
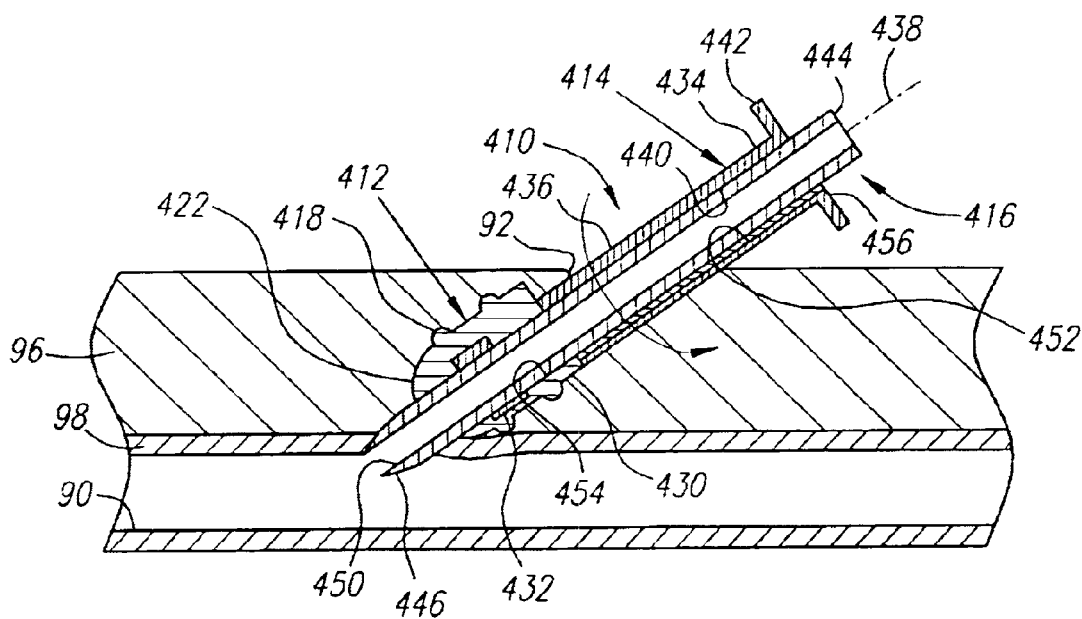

As shown in FIG. 7D, the apparatus 410 may be counter-rotated to withdraw the plug member 412 away from the wall 98 of the vessel 90. For example, bleed back may occur when the plug member 412 is within or in close proximity to the vessel 90, as shown in FIG. 7C. Rotation of the apparatus 410 may then be reversed, i.e., in a second direction opposite the first direction (indicated by exemplary arrow), to withdraw the plug member 412 a predetermined distance relative to the vessel 90, as shown in FIG. 7D. Because of the known pitch of the thread pattern 418, the distance that the plug member 412 is moved relative to the vessel 90 may be related directly to the number of rotations and/or partial rotations that the apparatus 410 is counter-rotated.

Figure 7E:
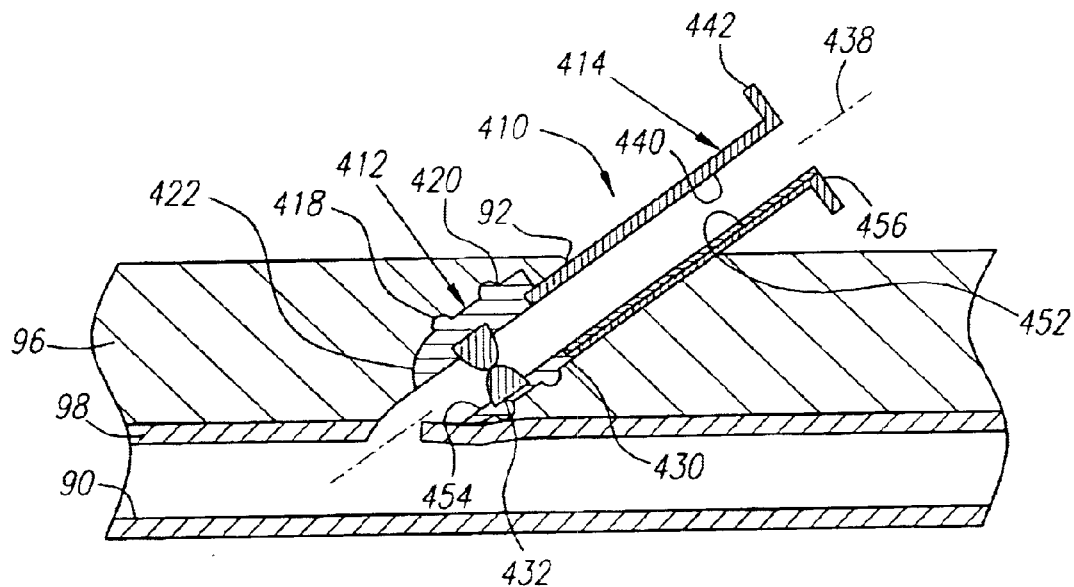

Once the desired deployment location is attained, the sheath 416 may be removed, as shown in FIG. 7E. Alternatively, the sheath 416 may be withdrawn earlier, e.g., when the distal end 422 of the plug member 412 is advanced into the vessel 90, or even earlier. As shown, the sealing member 432 may expand to substantially seal the lumen 424 in the plug member 412, similar to the embodiments described above. For example, the sealing member 432 may automatically expand when exposed to fluid, e.g., passing through the lumen 424. Alternatively, the sealing member 432 may be expanded to substantially seal the lumen 424, either by an actuator or by compression of the sealing member 432 (not shown), similar to the embodiments described above.

If desired, the bleed back port 454, e.g., if a separate lumen (not shown) from the lumen 424, may also include a sealing member (also not shown) for substantially sealing the bleed back port 454 from fluid flow therethrough, similar to the sealing members described above.

Figure 7F:
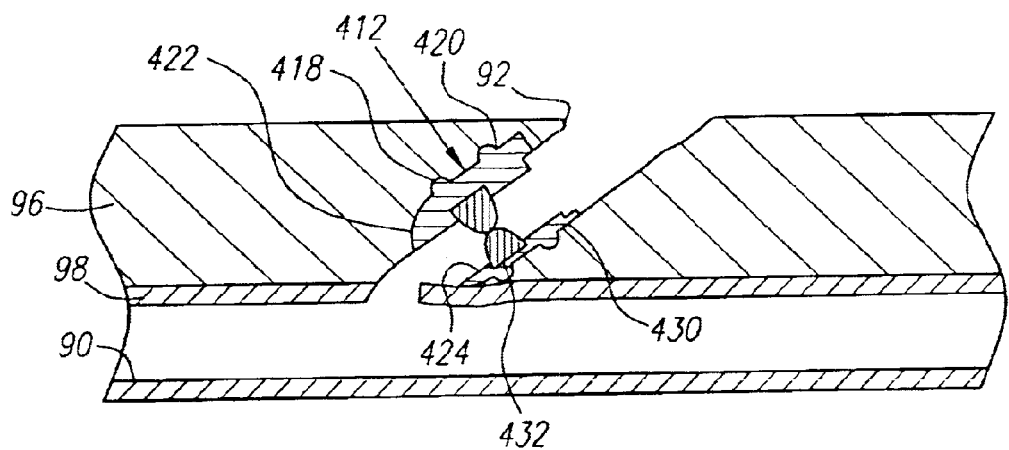

When the plug member 412 is disposed at a desired location within the passage 92 and/or once hemostasis is obtained, the plug member 412 may be released from the handle device 414. The handle device 414 (and sheath 416 if still within the passage 92) may be withdrawn from the passage 92. As shown in FIG. 7F, the plug member 412 may remain in place to substantially seal the passage 92, e.g., until the plug member 412 is absorbed by the patient's body. Alternatively, the plug member 412 may be retrieved once the tissue between the plug member 412 and the vessel 90 has substantially healed, as described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for sealing a passage through tissue, comprising:
   a bioabsorbable body comprising a proximal end, a distal end, and a helical thread on an outer surface extending at least partially between the proximal and distal ends, the body comprising a lumen extending between the proximal end and a distal inlet port; and
   a sealing member disposed within the lumen that is expandable across the lumen for substantially sealing the lumen from fluid flow therethrough.

2. The device of claim 1, wherein the sealing member comprises a material that is expandable when exposed to fluid to substantially seal the lumen.

3. The device of claim 2, wherein the material comprises an expandable gel foam.

4. The device of claim 1, wherein the sealing member comprises an annular-shaped member.

5. The device of claim 1, wherein the sealing member comprises a bioabsorbable material.

6. The device of claim 1, wherein the sealing member is biased towards a first configuration for substantially sealing the lumen from fluid flow therethrough, and is movable to a second configuration for accommodating introduction of one or more devices through the lumen.

7. The device of claim 1, further comprising a connector on the proximal end of the body for detachably securing the body to a delivery device.

8. The device of claim 1, further comprising an elongate shaft extending from the proximal end of the body.

9. The device of claim 1, wherein the body has a length of not more than about ten millimeters.

10. The device of claim 1, wherein the body has a diameter and a length, the diameter being not more than about twice the length.

11. A device for sealing a passage through tissue, comprising:
    a bioabsorbable body comprising a proximal end, a distal end, and a helical thread on an outer surface extending at least partially between the proximal and distal ends, the body comprising a lumen extending between a proximal port and a distal port, the lumen comprising a tapered portion that tapers in cross-section; and
    a sealing member comprising a generally annular-shaped member disposed adjacent a wide end of the tapered portion of the lumen, the sealing member being movable into the tapered portion for substantially sealing the lumen from fluid flow therethrough.

12. The device of claim 11, wherein the sealing member comprises a material that is expandable when exposed to fluid to substantially seal the lumen.

13. The device of claim 11, wherein the sealing member comprises a coil of material.

14. The device of claim 11, wherein the sealing member comprises a flexible material that may be wedged into the tapered portion.

15. The device of claim 11, wherein the sealing member comprises a bioabsorbable material.

16. The device of claim 11, further comprising a connector on the proximal end of the body for detachably securing the body to a delivery device.

17. The device of claim 11, further comprising an elongate shaft extending from the proximal end of the body.

18. The device of claim 11, wherein the body has a length of not more than about ten millimeters.

19. An apparatus for sealing a passage through tissue, comprising:
    an elongate member having a proximal end, a distal end, and a lumen extending between the proximal and distal ends; and
    a plug member disposed on the distal end of the elongate member, the plug member comprising a helical thread on its outer surface, the plug member comprising a distal port therein in communication with the lumen, the plug member having a cross-section larger than a cross-section of the elongate member.

20. The apparatus of claim 19, wherein the plug member comprises a passage therein extending between the distal port and the lumen.

21. The apparatus of claim 20, further comprising a sealing member disposed in the passage for substantially sealing the passage from fluid flow therethrough.

22. The apparatus of claim 21, wherein the sealing member comprises a material that is expandable when exposed to fluid for substantially sealing the passage.

23. The apparatus of claim 21, wherein the sealing member is biased towards a first configuration for substantially sealing the passage from fluid flow therethrough, and is movable to a second configuration for accommodating introduction of one or more devices through the passage.

24. The apparatus of claim 21, wherein the sealing member comprises a valve.

25. The apparatus of claim 21, wherein the lumen includes a tapered portion reducing in cross-section, and wherein the sealing member comprises a generally annular-shaped member disposed adjacent a wide end of the tapered portion of the lumen, the annular-shaped being movable into the tapered portion for substantially sealing the lumen.

26. The apparatus of claim 25, further comprising a activation element coupled to the elongate member, the activation element extending into the lumen of the plug member for moving the sealing member into the tapered portion for substantially sealing the lumen.

27. The apparatus of claim 20, further comprising an elongate member insertable through the lumen such that a distal end of the elongate member is disposed beyond the distal end of the plug member.

28. The apparatus of claim 27, wherein the distal end of the elongate member comprises a location indicator for identifying when the distal end of the plug member is disposed adjacent a body lumen.

29. The apparatus of claim 28, wherein the elongate member comprises a tubular member including a bleed back lumen, and wherein the location indicator comprises a bleed back port on the distal end of the tubular member, the bleed back port being in communication with the bleed back lumen.

30. The apparatus of claim 28, wherein the location identifier comprises an expandable member, the expandable member being expandable when the distal end is disposed within a body lumen for providing tactile feedback of a location of the distal end of the plug member with respect to the body lumen.

31. The apparatus of claim 27, wherein the elongate member comprises an obturator including a substantially atraumatic distal tip.

32. The apparatus of claim 27, further comprising a valve in the passage for substantially sealing the passage yet accommodating insertion of the elongate member therethrough.

33. The apparatus of claim 19, wherein the plug member is releasable from the elongate member.

34. The apparatus of claim 33, wherein the elongate member comprises an actuator for releasing the plug member from the distal end of the elongate member.

35. The apparatus of claim 33, further comprising cooperating connectors on the distal end of the elongate member and on the plug member for releasably securing the plug member to the distal end of the elongate member.

36. The apparatus of claim 33, wherein the plug member comprises an interior cavity, and wherein the elongate member comprises an engagement element extending from the distal end thereof for insertion into the cavity, the engagement element being expandable and collapsible for engaging and disengaging an interior wall of the plug member, thereby selectively securing the plug member to and releasing the plug member from the distal end of the elongate member, respectively.

37. The apparatus of claim 33, wherein the plug member comprises bioabsorbable material.

38. A method for sealing a passage through tissue communicating with a body lumen using an apparatus comprising an elongate member, a plug member disposed on a distal end of the elongate member, the plug member comprising an outer surface including a helical thread, and a bleed back indicator associated with a distal end of the plug member, the method comprising:

inserting the plug member into the passage;
rotating the elongate member, thereby threading the plug member into the passage until the bleed back indicator enters the body lumen, whereupon fluid from the body lumen may enter the bleed back indicator to identify the location of the body lumen with respect to the plug member; and
reversing rotation of the elongate member, thereby withdrawing the plug member a predetermined distance relative to the body lumen.

39. The method of claim 38, further comprising releasing the plug member from the elongate member within the passage.

40. The method of claim 39, wherein the plug member comprises a bioabsorbable material, and wherein the method further comprises leaving the plug member within the passage until it is absorbed by the tissue.

41. The method of claim 38, wherein the body lumen comprises a blood vessel, and wherein the elongate member is rotated until the plug member substantially seals at least one of the passage and a wall of the blood vessel.

42. The method of claim 41, further comprising:
leaving the plug member within the passage for sufficient time for hemostasis to occur; and
removing the plug member from the passage.

43. The method of claim 41, wherein the step of rotating the elongate member comprises threading the plug member through one or more intermediate layers of tissue towards the vessel.

44. The method of claim 43, wherein the one or more intermediate layers of tissue comprises a layer of fascia, the helical thread facilitating threading the plug member through the layer of fascia.

45. The method of claim 38, wherein the elongate member includes a lumen extending from its proximal end through the plug member.

46. The method of claim 45, wherein the bleed back indicator comprises a bleed back port in the plug member, the bleed back port being in communication with the lumen.

47. The method of claim 45, further comprising inserting an obturator through the lumen until a distal end of the obturator extends distally beyond the plug member.

48. The method of claim 47, wherein the bleed back indicator comprises a bleed back lumen in the obturator.

49. The method of claim 38, further comprising introducing one or more instruments through the passage to perform a procedure before inserting the plug member into the passage.

50. A method for sealing a passage through tissue communicating with a body lumen using an apparatus comprising an elongate member, a plug member disposed on a distal end of the elongate member, the plug member comprising an outer surface including a helical thread, and a lumen extending proximally from a distal port in the plug member, the method comprising:

inserting the plug member into the passage until the helical thread begins to enter the passage;
rotating the elongate member, thereby threading the plug member into the passage until the distal port enters the body lumen, whereupon fluid from the body lumen may enter the distal port to identify the location of the body lumen with respect to the plug member; and
activating a sealing member in the lumen, thereby substantially sealing the lumen from fluid flow therethrough.

51. The method of claim 50, further comprising reversing rotation of the elongate member, thereby withdrawing the plug member a predetermined distance relative to the body lumen.

52. The method of claim 50, further comprising releasing the plug member within the passage.

53. The method of claim 50, wherein the sealing member comprises a material that is expandable upon exposure to fluid, and wherein the activating step comprises exposing the sealing member to fluid when the distal port enters the body lumen.

54. A method for sealing a passage through tissue communicating with a body lumen, the method comprising:

provuding an elongate member extending through the passage into the body lumen;

advancing a plug member which is releasably disposed on the distal end of a handle device over the elongate member until a helical threat on an outer surface of the plug member begins to engage tissue surrounding the passage;

rotating the plug member, thereby threading the plug member into the passage until a distal port in the plug member enters the body lumen, whereupon fluid from the body lumen may enter the distal port to indicate that the plug member has entered the body lumen;

withdrawing the elongate member from the passage, leaving the plug member within the passage to substantially seal the passage; and releasing the plug member from the distal end of the handle device.

55. The method of claim 54, further comprising reversing rotation of the plug member prior to releasing the handle device, thereby withdrawing the plug member a predetermined distance relative to the body lumen.

56. The method of claim 55, wherein the one or more intermediate layers of tissue comprises a layer of fascia, the helical thread facilitating threading the plug member through the layer of fascia.

57. The method of claim 54, further comprising activating a sealing member within the lumen of the plug member, thereby substantially sealing the lumen from fluid flow therethrough.

58. The method of claim 54, wherein the rotating step comprises rotating the handle device, thereby rotating the plug member.

59. The method of claim 54, wherein the elongate member comprises an introducer sheath, and wherein the method further comprises inserting one or more devices through the introducer sheath into the body lumen.

60. The method of claim 54, wherein the step of rotating the elongate member comprises threading the plug member through one or more intermediate layers of tissue towards the body lumen.

61. A method for sealing a passage through tissue communicating with a body lumen, the method comprising:

providing an elongate member extending through the passage into the body lumen;

advancing a plug member over the elongate member until a helical thread on an outer surface of the plug member begins to engage tissue surrounding the passage;

rotating the plug member, thereby threading the plug member into the passage until a distal port in the plug member enters the body lumen, whereupon fluid from the body lumen may enter the distal port to indicate that the plug member has entered the body lumen;

reversing rotation of the plug member, thereby withdrawing the plug member a predetermined distance relative to the body lumen; and withdrawing the elongate member from the passage, leaving the plug member within the passage to substantially seal the passage.

* * * * *